US00PP24612P3

(12) United States Plant Patent
Weber

(10) Patent No.: US PP24,612 P3
(45) Date of Patent: Jul. 8, 2014

(54) STRAWBERRY PLANT NAMED 'WALKER'

(50) Latin Name: *Fragaria×ananassa*
Varietal Denomination: Walker

(75) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 47 days.

(21) Appl. No.: 13/573,230

(22) Filed: Aug. 31, 2012

(65) Prior Publication Data

US 2014/0068826 P1 Mar. 6, 2014

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — MacMillan, Sobanski & Todd, LLC

(57) ABSTRACT

This invention relates to a new and distinct June-bearing (short day responsive) strawberry plant named 'Walker' primarily adapted to the growing conditions of the west central New York and other regions of similar climate. The new plant is primarily characterized by longer than broad fruit, conical fruit shape, uniformity in shape between primary and secondary fruit, reflexed calyx, dark red-purple fruit color and glossy fruit skin.

5 Drawing Sheets

Genus and species: *Fragaria×ananassa.*
Variety denomination: 'Walker'.

BACKGROUND AND SUMMARY OF THE INVENTION

I. Field & Utility Summary

The present invention relates to a new and distinct variety of strawberry. The strawberry variety is primarily characterized by longer than broad fruit, conical fruit shape, uniformity in shape between primary and secondary fruit, reflexed calyx, dark red-purple fruit color and glossy fruit skin. Fruit of the new plant ripens after the plant 'Honeoye' (not patented), similar to the plant 'L'Amour' (U.S. Plant Pat. No. 16,480) and before 'MNUS 210' (U.S. Plant Pat. No. 10,191).

Test plantings in various locations at in New York, Illinois and Michigan have shown this plant to be widely adapted to differing soil and climactic conditions. It has shown cold hardiness typical to strawberries in a matted row system when covered with straw in the winter, which is standard procedure for this growing region.

The new plant is primarily adapted to the climate and growing conditions of west central NY, the upper mid-western U.S, the mid-Atlantic states and southeastern Canada. This region provides the necessary climate conditions required for it to produce a strong vigorous plant and to produce fruit in the summer harvest season from May to July, depending on location.

II. Cultivation Summary

'Walker' originated from hand-pollinated hybridization in 1997 in Geneva, N.Y.

III. Comparisons

NYUS299, the proprietary the female parent (unpatented), is June-bearing with smaller average fruit size (8.3 g) that is medium red, firm fleshed, and conic shaped that ripens in a similar season to 'Walker'.

NY1674, the proprietary male parent (unpatented), is a very vigorous plant with smaller average fruit size (8.1 g) that is dark red, globose shaped, moderately soft fleshed and ripens in a similar season to 'Walker'.

Other varieties which are believed to most closely resemble 'Walker' are 'Honeoye' (not patented), 'L'Amour' (U.S. Plant Pat. No. 16,480) and 'Jewel' (U.S. Plant Pat. No. 5,897).

In comparison to the similar plant 'Honeoye', 'Walker' differs by the following characteristics. The plant of 'Walker' is taller and more upright in growth habit with greater vigor. The fruit of 'Walker' is larger than that of 'Honeoye' with a more reflexed calyx. The fruit skin and flesh color of 'Walker' is darker red-purple than that of 'Honeoye'. The yield of 'Walker' is larger than that of 'Honeoye'. The fruit of 'Walker' is firmer with glossier skin than that of 'Honeoye'. The fruit of 'Walker' has lower soluble solids (% Brix) and equal titratable acids compared to 'Honeoye' with similar juice pH. The fruit of 'Walker' has higher anthocyanin content compared to 'Honeoye'. The harvest season of 'Walker' is later than that of 'Honeoye' and slightly less compact.

In comparison to the similar plant, 'L'Amour', 'Walker' differs by the following combination of characteristics. The plant of 'Walker' is shorter and smaller with more upright leaves. The leaflets are less wide and similar in length giving them a greater length to width ratio and an ovate shape. The stipules of 'Walker' are shorter and less wide than those of 'L'Amour'. The fruit of 'Walker' is smaller in size, with darker red-purple flesh color than 'L'Amour'. The fruit of 'Walker' has lower average soluble solids, higher titratable acids, lower juice pH and higher anthocyanin content than 'L'Amour'.

The flowering trusses of 'Walker' are shorter than those of 'L'Amour'. The flowers of 'Walker' are smaller in diameter than the flowers of 'L'Amour' with a greater petal length to width ratio than 'L'Amour'. The harvest season for 'Walker' is more compact than that of 'L'Amour'.

In comparison to the similar plant, 'Jewel', 'Walker' differs by the following combination of characteristics. The plant of 'Walker' is more vigorous but with shorter stature than 'Jewel'. The foliage is smaller in size with less interveinal leaf blistering. A pair of petiole bracts are occasionally present in 'Walker' and absent in 'Jewel'. The leaves are more sharply serrated in 'Walker' than 'Jewel'. The stipules of 'Walker' are shorter and less broad than those of 'Jewel'.

The fruit of 'Walker' is darker red-purple in color than 'Jewel' with more recessed seeds and a more reflexed calyx. The fruiting trusses of 'Walker' are shorter in overall length than 'Jewel'. The fruit of 'Walker' has lower soluble solids and higher titratable acidity than that of 'Jewel'. The fruit of 'Walker' has higher anthocyanin content than the fruit of 'Jewel'.

Strawberry plant 'Walker' has these distinguishing characteristics;

1. Vigorous plants with an upright growth habit and moderate stolon production;
2. Trifoliate leaves with a flat appearance and gray green undersides and ovate leaflets with greater length than width;
3. Longer than broad fruit, conical fruit shape, dark red-purple fruit color, dark red-purple flesh color that is lighter towards the center, high fruit gloss and moderately soft flesh firmness;
4. Reflexed calyx generally equal or smaller in diameter than the fruit width;
5. Medium length pedicels and peduncles with few bracts;
6. Mid-season production with high yields; and
7. Compact harvest season.

IV. Breeding History

'Walker' originated from a hand-pollinated hybridization made in 1997 in Geneva, N.Y. between female parent NYUS299 (not patented)×male parent NY1674 (not patented). Both parents of 'Walker' are hybrids of the strawberry genus of the species *Fragaria×ananassa*. Thus 'Walker' is of the species *Fragaria×ananassa* Duchesne. The seeds resulting from this controlled hybridization were germinated in a greenhouse in Geneva, N.Y. during the winter of 1997-98. Resulting seedlings were planted in the spring of 1998 in Geneva, N.Y. The seedlings fruited in the summer of 1999 and one, designated NY99-15, was selected for its attractive, dark red-purple fruit and strong strawberry flavor.

V. Asexual Reproduction

During 1999, the original plant selection NY99-15 was propagated asexually by stolons (runners) at Geneva, N.Y. and a test planting of ten plants was established. Subsequently, larger test plantings were established with asexually multiplied plants at Geneva, N.Y. The new plant NY99-15 was re-designated 'Walker' and tested over the next several years in the fruiting fields at Geneva, N.Y. Further propagation was done using tissue culture in Geneva, N.Y. to produce disease free material for use in further testing. Tissue culture plants were used as mother plants for propagation from stolons.

VI. Stability

Asexual propagation has demonstrated that the combination of traits disclosed herein as characterizing the strawberry plant 'Walker' are fixed and remain true to type through successive generations of asexual reproduction. All propagules of 'Walker' have been observed to be true to type in that during all asexual multiplication, the vegetative and fruit characteristics of the original plant have been maintained. All plants planted from dormant crowns or rooted runner tips have fruited after one season of growth in the field.

BRIEF DESCRIPTION OF THE FIGURES

The accompanying color photographs show typical specimens of the new plant at various stages of development as nearly true as it is possible to make in color reproductions. The depicted plant and plant parts were from the first harvest season, approximately 13 months after planting.

DETAILED BOTANICAL DESCRIPTION OF THE INVENTION

Figure 1A:
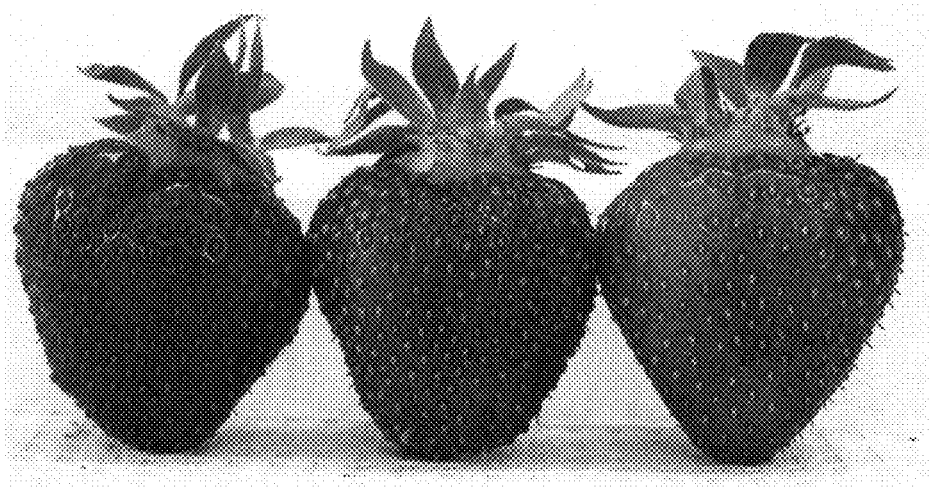
FIG. 1A-FIG. 1B shows typical external fruit characteristics of 'Walker' (A) including calyx structure and fruit shape compared to 'Jewel' (B) on Jun. 6, 2012.
Figure 1B:
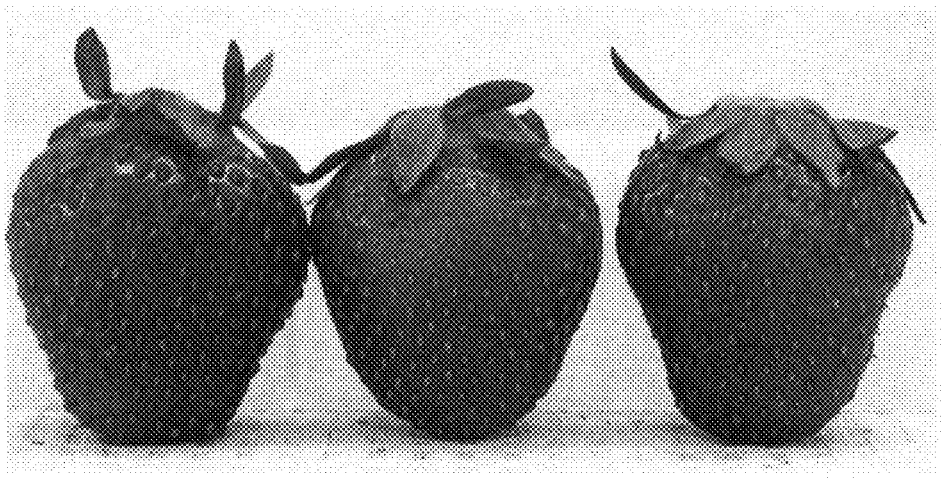
Figure 2A:
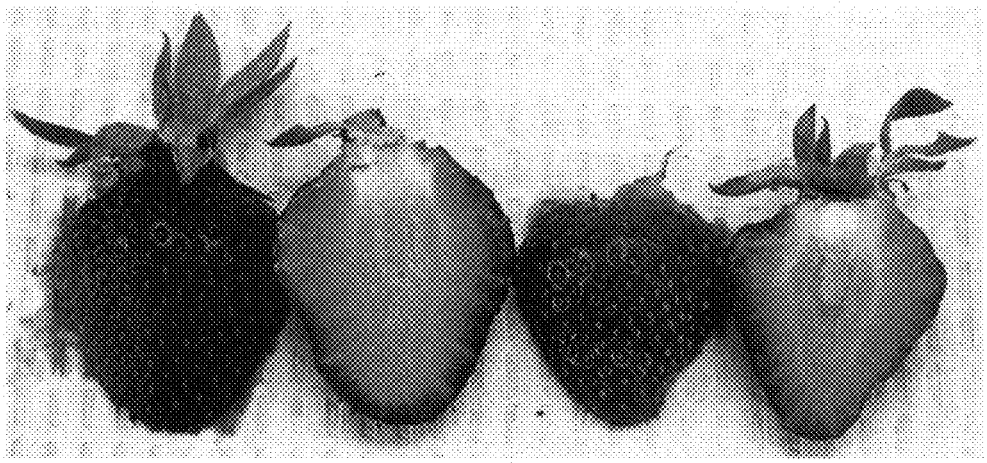
FIG. 2A-FIG. 2B shows typical internal fruit characteristics of 'Walker' (A) compared to 'Jewel' (B) on Jun. 6, 2012.
Figure 2B:
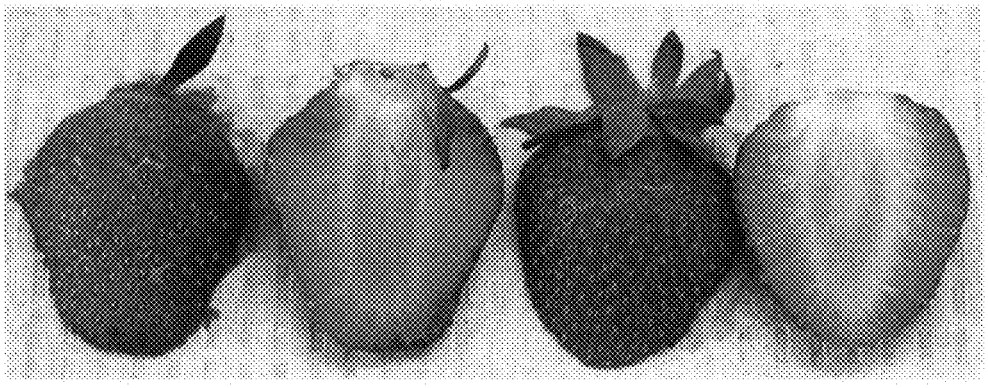
Figure 3A:
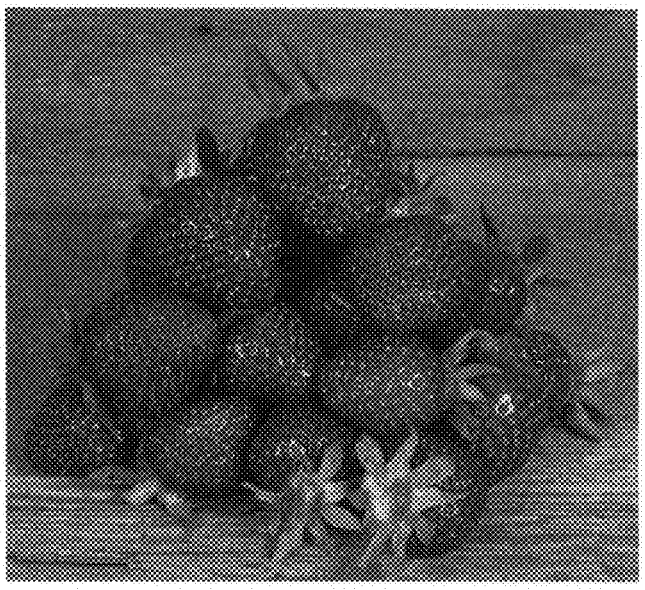
FIG. 3A-FIG. 3B shows typical external color of 'Walker' (A) compared to 'Jewel' (B).
Figure 3B:
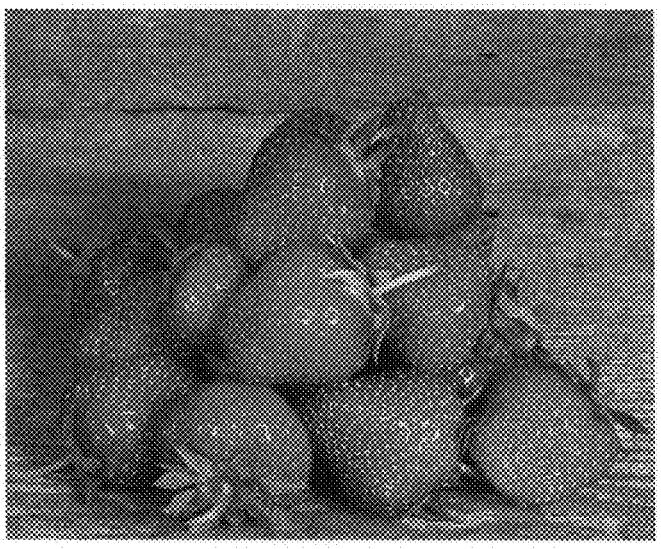
Figure 4A:
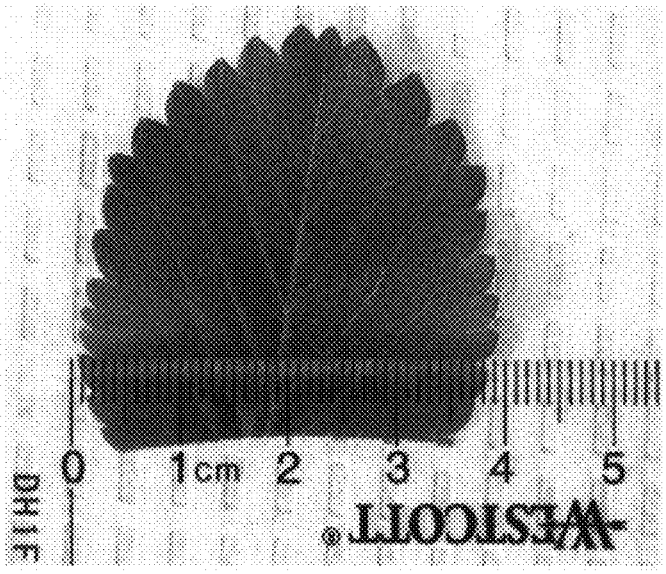
FIG. 4A-FIG. 4C shows leaf margin serrations for 'Walker' (A), 'Jewel' (B) and 'L'Amour' (C).
Figure 4B:
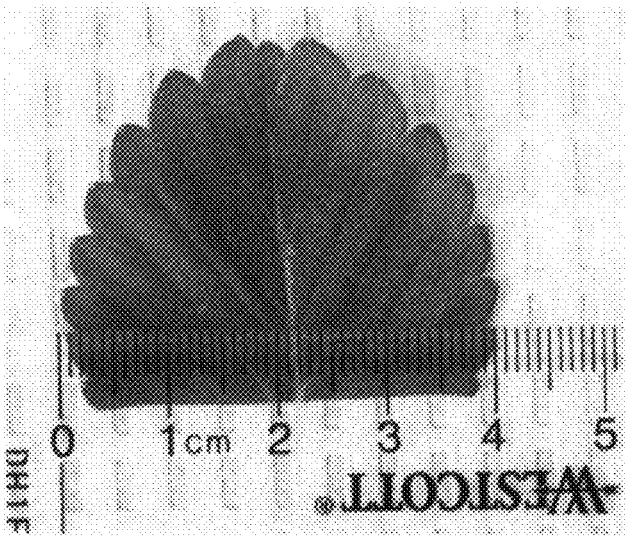
Figure 4C:
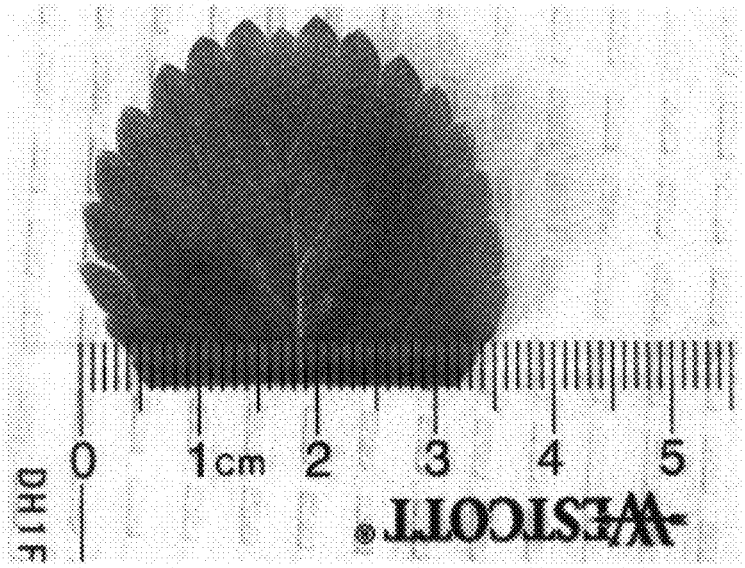

The following description of 'Walker' unless otherwise noted, is based on observations taken during the 2012 growing season in Geneva, N.Y. These measurements and ratings were taken from plants planted in May 2011. The age of the planting is approximately 13 months and in its first harvest season. Yield observations and fruit quality characteristics are averaged from data collected during the 2003-04 and 2008-10 production seasons. The characteristics of the new plant may vary in detail, depending upon variations in environmental factors (temperature, rainfall, humidity and light intensity). 'Walker' has not been observed under all possible environmental conditions. Color terminology where noted follows The Royal Horticultural Society Colour Chart, London.

Comparative Fruit Characteristics

'Walker' fruit, fruit production and fruit quality characteristics. Fruit characteristics are taken from the first harvest season.

TABLE 1

Fruit characteristics: Yield
Total fruit yield of 'Walker' and similar varieties from 2 separate trials, one harvested in 2003-04 and one in 2008-09 in Geneva, NY. Fruit was harvested in June in each year. The plants of 'Walker' were grown in Geneva, NY. The other varieties were grown in a nursery in South Deerfield, Mass. All plants were planted in May prior to the first harvest year for both trials.

| Cultivar (kg per ha) | 2003 | 2004 | 2008 | 2009 | Average |
|---|---|---|---|---|---|
| 'Walker' | 8,740 | 24,790 | 4,910 | 20,010 | 14,610 |
| 'Honeoye' | 11,730 | 17,160 | 3,990 | 7,970 | 6,360 |
| 'L'Amour' | 7,090 | 14,490 | — | — | 10,790 |
| 'Jewel' | 11,160 | 15,440 | 11,270 | 5,760 | 10,910 |

TABLE 2

Fruit Characteristics: Weight
Average fruit weight of 'Walker' and similar varieties from 2 separate trials, one harvested in 2003-04 and one in 2008-09 in Geneva, NY. Fruit was harvested in June in each year. The plants of 'Walker' were grown in Geneva, NY. The other varieties were grown in a nursery in South Deerfield, Mass. All plants were planted in May prior to the first harvest year for both trials.

| Cultivar (g per berry) | 2003 | 2004 | 2008 | 2009 | Average |
|---|---|---|---|---|---|
| 'Walker' | 10.8 | 10.6 | 10.7 | 11.2 | 10.8 |
| 'Honeoye' | 13.2 | 10.0 | 9.5 | 9.2 | 10.5 |
| 'L'Amour' | 11.9 | 11.7 | — | — | 11.8 |
| 'Jewel' | 10.9 | 10.6 | — | 11.1 | 10.9 |

TABLE 3

Fruit Characteristics: Color
Comparison of secondary fruit characteristics of 'Walker', with standards from Geneva, NY.

| Character | 'Walker' | 'L'Amour' | 'Jewel' | 'Honeoye' |
|---|---|---|---|---|
| RHS Exterior Color Mature Fruit | red-purple 59A | red 46B | red 44A | red 46A |
| Fruit Length mean (cm) | 3.68 | 4.22 | 3.46 | 3.85 |
| Fruit Width mean (cm)[1] | 3.49 | 3.62 | 3.61 | 3.55 |
| Fruit Length/Width Ratio | 1.05 | 1.20 | 1.05 | 1.08 |
| No. Sepals/Berry | 10.0 | 11.0 | 12.4 | 12.7 |

[1]Width is measured across the widest part of the berry, typically across the shoulders.

TABLE 4

Fruit Characteristics: Quality
Comparison of 2010 fruit quality characteristics including soluble solids (% Brix), titratable acidity, juice pH and anthocyanin content of 'Walker', with standards from Geneva, NY.

| Character | 'Walker' | 'L'Amour' | 'Jewel' | 'Honeoye' |
|---|---|---|---|---|
| Soluble solids[1,2] | 9.03 | 10.37 | 11.77 | 10.93 |
| Titratable acidity[2,3] | 9.29 | 9.64 | 10.93 | 10.89 |
| Juice pH[2] | 3.38 | 3.50 | 3.38 | 3.42 |
| Anthocyanin content[2,4] | 306 | 117 | 147 | 148 |

[1]soluble solids is estimated from % Brix with % Brix being an indirect measurement of the sugar content in the fruit
[2]Averaged from 3 samples on 3 dates during the harvest season.
[3]g per L equivalents of citric acid
[4]mg/100 g fresh weight

TABLE 5

Fruit Characteristics: Details

| Characteristic | Description |
|---|---|
| Ratio of length/width | Longer than broad |
| Size | Medium to large |
| Predominant shape | Conical |
| Difference in shapes between primary and secondary fruit | Little to none |
| Band without achenes | Intermediate width |
| Color of mature fruit | Bright to dark red |
| Evenness of color | Very even |
| Glossiness | Strong |

TABLE 5-continued

Fruit Characteristics: Details

| Characteristic | Description |
|---|---|
| Insertion of achenes | Level to slightly recessed from surface |
| Attitude of the calyx segments | Somewhat reflexed up |
| Size of calyx in relation to fruit diameter | 2.3 cm to 4.0 cm |
| Adherence of calyx (when fully ripe) | Strong |
| Firmness of skin | Moderately firm |
| Color of flesh | Dark purple-red with lighter ring (red-purple 59A to red 44A in center) |
| Distribution of red color of the flesh | Throughout the flesh with the darkest flesh around internal margin and lighter towards the center |
| Hollow center | Moderately to strongly expressed |
| Seed color | Medium yellow-green to dark red-purple (yellow-green 151D to red-purple 59A). |
| Time of flowering (50% of plants at first flower) | Medium to early |
| Time of ripening (50% of plants with first ripe fruit) | Medium to early |
| Type of bearing | Fully short day responsive |
| Avg. number of achenes | 240 per fruit |
| Achene position | Indented in the flesh so that the upper surface of the achene is even to slightly extruded above the flesh surface |
| Presence of hollow core | Common, often with pithy flesh within the space |
| Hollow core length | 5 to 15 mm |
| Hollow core width | 5 to 7 mm |

Plant Characteristics

'Walker' plant characteristics. Plant characteristics are taken from a fully mature mid-season plant.

TABLE 6

Plant Characteristics: Comparisons
Comparison of plant characteristics of 'Walker', with standards from Geneva, NY Jun. 22, 2012.

| Character | 'Walker' | 'L'Amour' | 'Jewel' |
|---|---|---|---|
| Plant Height mean (cm) | 26.0 | 31.9 | 27.3 |
| Vigor[1] | 8.0 | 8.3 | 5.0 |
| Canopy density[1] | 7.5 | 7.7 | 7.0 |

[1]Rated on a scale of 1-9 (9 being more vigorous or dense) in mature replicated plots.

TABLE 7

Plant Characteristics: Details

| Characteristic | Description |
|---|---|
| Size | Medium |
| Habit | Upright |
| Density | High |
| Vigor | Strong |

Foliage Characteristics

'Walker' foliage characteristics. Foliage characteristics are taken from a fully mature tri-foliate leaf during mid season.

TABLE 8

Foliage Characteristics: Comparisons
Comparison of leaf characteristics of 'Walker', with standards from Geneva, NY on Jun. 22, 2012.

| Character | 'Walker' | 'L'Amour' | 'Jewel' |
|---|---|---|---|
| RHS Color (upper surface) | green 137A | green 137A | green 138A |
| RHS Color (lower surface) | greyed-green 191A | green 139C | green 137D |
| Terminal Leaflet Length mean (cm) | 7.4 | 8.4 | 7.5 |
| Terminal Leaflet Width mean (cm) | 5.7 | 8.5 | 7.6 |
| Terminal Leaflet ratio (L/W) | 1.29 | 0.99 | 0.99 |
| Petiole Length mean (cm) | 21.1 | 22.8 | 19.9 |
| Serrations/Leaf | 26.9 | 22.3 | 18.3 |
| Stipule Length mean (cm) | 1.6 | 3.5 | 3.0 |
| Stipule Width mean (cm) | 0.6 | 0.8 | 0.8 |

TABLE 9

Foliage Characteristics: Details

| Characteristic | Description |
|---|---|
| Color of upper surface | Medium to dark green |
| Color of under side | Medium to light grey-green |
| Shape in cross section | Slightly concave |
| Interveinal blistering | Light to moderate |
| Glossiness | Low, flat coloring |
| Number of leaflets/leaf | Generally three |
| Terminal leaflet size | Small to medium |
| Terminal leaflet - length/width ratio | Longer than broad |
| Terminal leaflet - shape of base | Cuneate |
| Terminal leaflet - shape serrations | Acute |
| Petiole - pubescence density | High |
| Petiole - stipule color | Light to medium yellow-green (yellow-green N144C) |
| Petiole - anthocyanin coloration of stipule | Slight blush of Red 45D |
| Petiole - attitude of hairs | Strongly upward towards leaf |
| Petiole - size of bract leaflets | Small |
| Petiole - frequency of bract leaflets | Approximately 10% of the petioles |
| Avg. number of leaflets | 3 |
| Venation pattern of leaflets | reticulated |

Flower and Inflorescence Characteristics

'Walker' inflorescence and flower characteristics. Inflorescence characteristics are taken from a fully mature plant during full bloom. Flower characteristics are taken from a secondary flower during mid season at full maturity:

TABLE 10

Flower and Inflorescence Characteristics: Comparisons
Comparison of inflorescence and secondary flower characteristics of 'Walker', with standards from Geneva, NY on May 10, 2012.

| Character | 'Walker' | 'L'Amour' | 'Jewel' |
|---|---|---|---|
| Fruiting Truss Length[1] mean (cm) | 21.6 | 32.3 | 20.9 |
| Corolla Diameter mean (mm) | 35 | 36 | 31 |
| Calyx Diameter mean (mm) | 33 | 33 | 34 |
| Petal Length mean (mm) | 14.8 | 15.4 | 14.0 |
| Petal Width mean (mm) | 13.3 | 13.6 | 13.3 |
| Petal L/W Ratio | 1.09 | 1.13 | 1.09 |
| Petals/Flower (mean) | 5.8 | 5.1 | 6.3 |
| Sepals/Flower (mean) | 10.0 | 11.0 | 12.4 |
| Petal shape | obovate | | |
| Petal RHS color | white 155C both surfaces | | |
| Shape of Apex | rounded | | |
| Shape of base | cuneate | | |
| Shape of margin | entire (not serrated) | | |

[1]as measured from the base of the primary peduncle where it attaches to the crown of the plant to the furthest berry.

TABLE 11

Inflorescence Characteristics: Details

| Characteristic | Description |
|---|---|
| Position relative to foliage | Even with canopy |
| Fruiting truss length | Medium |

TABLE 12

Flower Characteristics: Details

| Characteristic | Description |
|---|---|
| Color | White (white 155C). |
| Size | Medium to large |
| Size of calyx relative to corolla | Equal to smaller |
| Relative position of petals | No overlap when fully open |
| Petal length/width ratio | Longer than broad |
| Petal shape | Obovate |
| Sepal RHS color | Green 137D |
| Avg. sepal length | 8.5 cm |
| Avg. sepal width at base | 3.4 mm |

Pest reactions: It is known to be moderately resistant to the two-spotted spider mite and susceptible to aphids and flower thrips. It is susceptible to leaf spot, scorch and blight. It is resistant to powdery mildew. The susceptibility of the new plant to any of the virus complexes of NY has not been determined.

We claim:

1. A new and distinct strawberry plant cultivar as herein described and illustrated.

* * * * *